United States Patent [19]

Inami et al.

[11] Patent Number: 5,298,426

[45] Date of Patent: Mar. 29, 1994

[54] METHOD OF DIFFERENTIATING ERYTHROBLASTS FROM OTHER CELLS BY FLOW CYTOMETRY

[75] Inventors: Keiichi Inami; Hideaki Matsumoto, both of Hyogo, Japan

[73] Assignee: TOA Medical Electronics Co., Ltd., Japan

[21] Appl. No.: 790,598

[22] Filed: Nov. 7, 1991

[30] Foreign Application Priority Data

Feb. 22, 1991 [JP] Japan .................. 3-028521

[51] Int. Cl.$^5$ ............................................. G01N 1/30
[52] U.S. Cl. ............................................. 436/63; 435/6; 436/10; 436/172
[58] Field of Search ............... 436/63, 172, 10; 435/6, 435/63

[56] References Cited

U.S. PATENT DOCUMENTS

| | | | |
|---|---|---|---|
| 3,916,205 | 10/1975 | Kleinerman | 250/461 |
| 4,485,175 | 11/1984 | Ledis et al. | 436/63 |
| 4,499,183 | 2/1985 | Sujansky et al. | 435/6 |
| 4,751,188 | 6/1988 | Valet | 436/10 |
| 4,978,624 | 12/1990 | Cremins et al. | 436/63 |
| 5,039,613 | 8/1991 | Matsuda et al. | 436/172 |
| 5,047,321 | 9/1991 | Loken et al. | 436/172 |

FOREIGN PATENT DOCUMENTS 0268766  6/1988  European Pat. Off. .
86/01293  2/1986  PCT Int'l Appl. .

*Primary Examiner*—James C. Housel
*Assistant Examiner*—Ramon Torres
*Attorney, Agent, or Firm*—Pearne, Gordon, McCoy & Granger

[57] ABSTRACT

A method which comprises using a specified dye taken up by erythrocytic nucleated cells so that their nuclei are stained and can be readily differentiated from other cells by measurement with a flow cytometer is disclosed. The method relies basically upon flow cytometry by two-step staining that uses a first fluid that is an acidic hypotensive fluorescent dye solution and a second fluid that is a solution that changes the osmorality and pH of the first fluid. The first fluid further contains a fluorescent dye that diffuses into erythroblasts to specifically stain their nuclei, and a group of erythroblasts is separated from other cell groups on the two-dimensional plot constructed with the flow cytometer, whereby the results of erythroblast differentiation are computed.

6 Claims, 6 Drawing Sheets

METHOD OF DIFFERENTIATING ERYTHROBLASTS FROM OTHER CELLS BY FLOW CYTOMETRY

BACKGROUND OF THE INVENTION

1. Field of the Invention

This invention relates to a method of differentiating and counting erythroblasts with a flow cytometer.

2. Prior Art

Unexamined Published Japanese Patent Application No. 134958/1988 discloses a two-step staining process that uses a hypotonic acidic fluorescent dye solution and a solution that will changes its osmolarity and pH. A blood sample stained with those solutions is loaded in a flow cytometer to obtain signal for fluorescence and side-scattered light and on the basis of those signals, a two-dimensional plot of fluorescence intensity vs the intensity of side-scattered light is constructed, whereby the leukocytes in the sample are classified into five types: lymphocytes, monocytes, neutrophils, eosinophils, basophils and a noise component, respectively.

Unexamined Published Japanese Patent Application No. 134958/1988 does not mention the differentiation and counting of erythroblasts. Erythroblasts are cells ancestral to red corpuscles and they normally occur in the bone marrow but not in circulating blood. However, in certain diseases such as anemia and leukemia, erythroblasts also occur in circulating blood. Therefore, it is of clinical importance to measure erythroblasts.

SUMMARY OF THE INVENTION

The present invention has been accomplished in order to improve the method described in Unexamined Published Japanese Patent Application No. 134958/1988 and has as an object of providing a method that is capable of differentiating erythroblasts from other cells.

Erythrocytic cells have the capability of adjusting their own osmolarity by allowing water to come in or go out through the cell membranes in accordance with the osmolarity of the cell suspension. If the cell suspension has a lower osmolarity than the cells, they let water in through the cell membranes; if, on the other hand, the cell suspension has a higher osmolarity than the cells, they let water out through the cell membranes.

The method of the present invention takes advantage of that character of erythroblasts and has a specified dye taken up by erythrocytic nucleated cells so that their nuclei are stained and can be readily differentiated from other cells by measurement with a flow cytometer.

The method of the present invention for differentiating erythroblasts from other cells relies basically upon flow cytometry by utilizing a two-step staining method using a first fluid that is an acidic hypotensive fluorescent dye solution, and a second fluid that is a solution that changes the osmorality and pH of the first fluid. In accordance with the present invention, the first fluid further contains a fluorescent dye that diffuses into erythroblasts to specifically stain their nuclei, and a group of erythroblasts is separated from other cell groups on a two-dimensional plot constructed with the flow cytometer, whereby the results of erythroblast differentiation are computed.

Stated specifically, the present invention relates to a method of differentiating erythroblasts from other cells by flow cytometry which comprises the following steps (a) to (e):

(a) mixing blood with a hypotonic first fluid comprising a dye that is a fluorescent dye capable of diffusing into erythroblasts to stain their nuclei and a buffer for maintaining a pH in the acidic range;

(b) mixing the sample solution obtained in step (a) with a second fluid comprising a buffer that neutralizes the acid in the first fluid for maintaining the pH of the solution at a staining pH and an osmolarity adjusting agent for adjusting the osmolarity of the solution to a value at which the leukocytes remain unchanged in shape;

(c) loading the thus prepared sample solution in a flow cytometer and obtaining more than one signal for parameters including fluorescence and scattered light in association with individual cell types;

(d) constructing a two-dimensional plot of the intensities of fluorescence and scattered light from the detected signals; and (e) setting the distribution zone of erythroblasts on the constructed two-dimensional plot and counting the number of cells in that zone.

DETAILED DESCRIPTION OF THE INVENTION

The dyes that can be used in the first fluid in accordance with the present invention are listed below:

Eosinophil/basophil-staining dye:
  Astrazon Yellow 3G;
  Basic Yellow
Leukocyte-staining dye:
  Acridine Red;
  Rhodamine S;
  Rhodamine 6G;
  Rhodamine B;
  Rhodamine 19 perchlorate;
  Rhodamine 123;
  Eosin Y;
  Cyanosine;
  Cresyl Fast Violet;
  Darrow Red;
  Acronol Phloxine FFS;
  1,1'-dimethylthiocarbocyanine;
  1,1'-diethylthiocarbocyanine;
  1,1'-diethyl-9-methylthiocarbocyanine bromide;
  2-[γ-(1'-ethyl-4',5'-benzothiazolylidene)propenyl]-1-ethyl-4,5-benzoxazolium iodide;
  Astrazon Red 6B;
  C.I. Basic Violet 16;
  2-(p-dimethylaminostyryl)-1-ethyl-4,5-benzothiazolium iodide;
  2,4-bis(p-dimethylaminostyryl)-1-ethylpyridinium iodide;
  2,6-bis(p-dimethylaminostyryl)-1-ethylpyridinium iodide;
  Astrazon Orange R
Erythroblast B-staining dye:
  Propidium iodide;
  Etidium bromide;
  M-264.

The first and second fluids to be used in the method of the present invention preferably satisfy the following conditions:

(a) Dye concentration

Dyes need to be contained in the first fluid at such concentrations that their final concentrations obtained by mixing the first and second fluids will lie within the ranges set forth below.

Basic Yellow 11 and Astrazon Orange R are commercial products that are available from Aldrich Chemical Company, Inc. and Tokyo Kasei K. K., respectively.

If the concentration of Basic Yellow 11 is above a certain level, the intensity of fluorescence from basophils is higher than that from the other types of leukocytes, and the intensity of fluorescence from eosinophils also increases at higher concentrations. The intensities of fluorescence from lymphocytes, neutrophils and monocytes are virtually independent of the concentration of Basic Yellow 11. Hence, in order to differentiate basophils and eosinophils from the other types of leukocytes in terms of the intensity of fluorescence, the concentration of Basic Yellow 11 may be adjusted to 70-100 ppm and higher.

Separation between noise and the intensity of fluorescence from lymphocytes/neutrophils is possible at Astrazon Orange R concentrations of 100 ppm and above, and good separation can be achieved at concentrations of 200 ppm and above. At concentrations of 300 ppm and above, the efficiency of separation substantially levels off and the intensities of fluorescence from basophils and eosinophils will decrease slightly. Therefore, the concentration of Astrazon Orange R is preferably at 300 ppm or in its neighborhood for achieving efficient separation of leukocytes from noise.

Propidium iodide is a commercial product available from Sigma Chemical Co. If the concentration of Propidium iodide is 2.5 μg/ml (2.5 ppm) and below, its staining power is so small that efficient separation between erythroblasts and leukocytes cannot be achieved in two-dimensional plots. If the concentration of Propidium iodide is 100 μg/ml and above, the S/N ratio of signal detection decreases (the difference between a fluorescence signal and the background becomes so small as to prevent effective signal detection). The same discussion may apply to the concentration of Etidium bromide.

(b) pH of the first fluid

In order to lyse erythrocytes, the pH of the first fluid is preferably set at 5.0 and below but in order to prevent coagulation of platelets, the pH of the first fluid must be at least 3.5.

(c) Buffer in the first fluid

Any buffer that has a pKa value of approximately 4.5, such as citrate, maleate and diglycolate, may be employed in the first fluid. As for diglycolic acid, the intensity of fluorescence from basophils will decrease slightly if the concentration of diglycolic acid is 5 mM and below. On the other hand, the lysing of erythrocytes will be insufficient if the concentration of diglycolic acid is 50 mM and above. An optimum concentration of diglycolic acid is about 10 mM.

(d) Osmolarity of the second fluid

There will be no change in the separation pattern even if the final osmolarity of the dye solution is varied from 167 to 387 mOsm/kg by changing the amount of an osmolarity compensating agent (e.g. sodium chloride) added to the second fluid. It is recommended that the osmolarity of the second fluid be adjusted in such a way that the final osmolarity of the dye solution is at an approximately isotonic value (280 mOsm/kg).

(e) Buffer in the second fluid

Any buffer that has a pKa value in an approximate range of 8.5 to 9.0, such as borate, Tris and tricin, may be employed in the second fluid. If tricin is used, the intensity of fluorescence from basophils and eosinophils decreases at a tricin concentration of 50 mM and below. A preferred concentration of tricin is ca. 300 mM.

In accordance with the present invention, not only a fluorescence signal but also a side-scattered light signal is produced from leukocytes. The fluorescence signal reflects the cytochemical characters of leukocytes and depending on the interaction between stains and individual leukocyte types, signals of different intensities are produced from the leukocytes. The side-scattering light signal reflects the structural information of an individual white cell. The larger the nucleus of a white blood cell and the more granules that are present in it, the greater the light reflection which will occur in the cell to produce a more intense side-scattered light. A lymphocyte contains very few or no granules, so the scattered light produced from the lymphocyte is the weakest of all leukocytes. On the other hand, a neutrophil contains many granules and has a large nucleus, so it produces more intense scattered light. Eosinophils produce scattered light the intensity of which is comparable to that produced from neutrophils. Monocytes and basophils produce scattered light having an intensity intermediate between those of scattered light from lymphocytes and neutrophils.

Therefore, as will be described below in detail, by combining a fluorescence signal with a side-scattered light signal, leukocytes can be classified into five types in accordance with the present invention.

Figure 1:
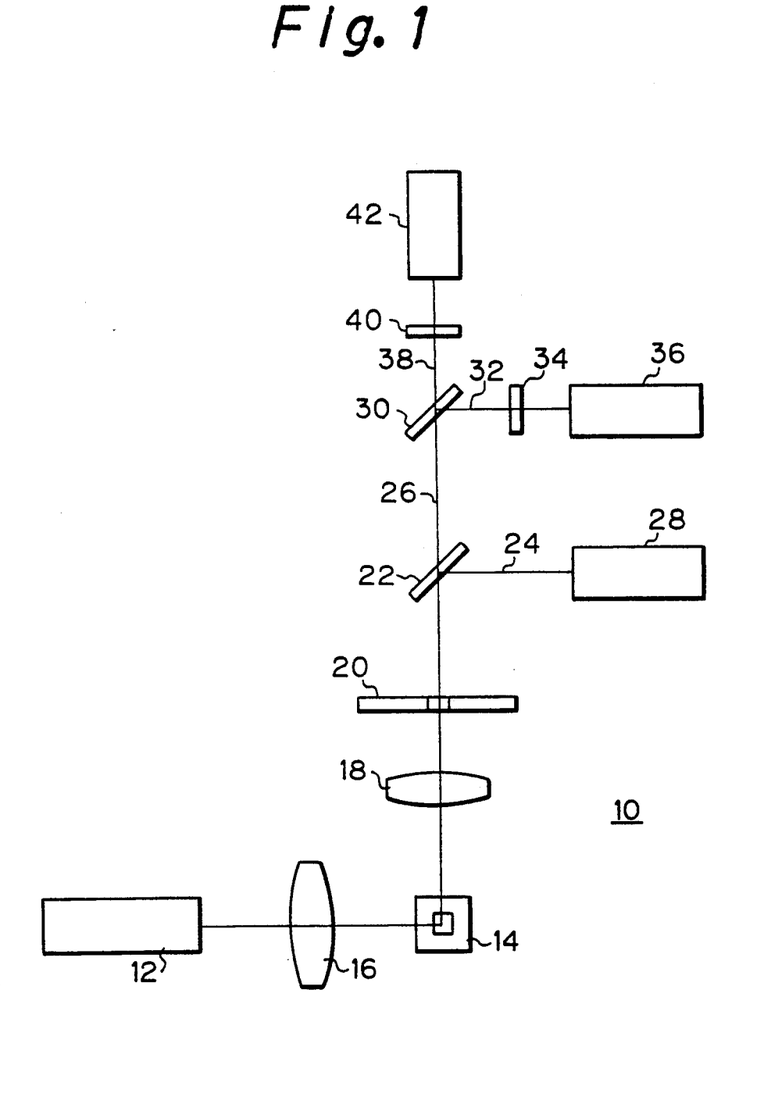
FIG. 1 is a schematic diagram of the optics of a flow cytometer that may be employed in implementing the method of the present invention.

A specific example of the optics of a flow cytometer employed in the present invention is hereunder described with reference to FIG. 1. The optics shown in FIG. 1 is used in a flow cytometer designed for measuring side-scattered light, red fluorescence and green fluorescence. The optics generally indicated by 10 uses an argon ion laser 12 as a light source and it operates at a wavelength of 488 nm, producing an output of 10 mW. Light emitted from the laser 12 is converged by a cylindrical lens 16 and illuminates a blood sample flowing through a flow cell 14.

When the stained leukocytes in the sample are irradiated by the laser light, they produce scattered light and fluorescence. The side scattered light and the fluorescence are converged with a condenser lens 18 and pass through an aperture 20 to fall upon a dichroic mirror 22. The dichroic mirror 22 reflects the side scattered light 24 and transmits the fluorescence 26. The side-scattered light 24 reflected from the dichroic mirror 22 is detected in a photomultiplier tube 28. Of the two kinds of fluorescence 26 that passes through the dichroic mirror 22, red fluorescence 32 is reflected by a dichroic mirror 30 and green fluorescence 38 is transmitted through that mirror. The reflected red fluorescence 32 passes through a color filter 34 and is detected in a photomultiplier tube 36. The transmitted green fluorescence 38 passes through a color filter 40 and is detected in a photomultiplier tube 42.

Erythrocytes in the blood sample emit only fluorescence of a very low intensity, so if it is only required to measure the intensity of fluorescence, erythrocytes will not interfere with the counting of leukocytes even if coincidence of erythrocytes and leukocytes occurs (i.e., erythrocytes and leukocytes pass through the detecting portion simultaneously). However, erythrocytes which produce scattered light having an intensity comparable to that of the scattered light emitted from leukocytes will interfere with the counting of leukocytes. In this case, one may measure fluorescence and scattered light simultaneously and regard as leukocytes only the corpuscles that emit fluorescence having an intensity greater than a certain level. However, if coincidence of leukocytes and erythrocytes occurs, the scattered light from erythrocytes is superimposed on the scattered light from leukocytes, thereby making accurate measurement of scattered light from the leukocytes impossible. In the optics 10 of a flow cytometer shown in FIG. 1, a blood sample is permitted to flow through the flow cell 14 after it has been diluted by, for example, 20 fold so that the probability of coincidence of erythrocytes and leukocytes is reduced and the potential interference by erythrocytes is decreased to a level that can be disregarded for practical purposes.

The first fluid to be used in the method of the present invention has a low osmorality. Hence, if a blood sample is suspended in the first fluid, the erythrocytic cells in the sample will swell upon absorbing water. As a result, the tissue of their cell membrane becomes loose thus causing the contents to leak out. Since mature erythrocytes have no nuclei, only their membrane is left to yield "ghosty" erythrocytes. Erythroblasts will swell in the same manner and their contents will leak out. However, erythroblasts have nuclei which remain intact in the membrane. The erythroblast dye diffuses into erythroblasts to stain their nuclei.

Unlike erythrocytic cells white blood cells do not permit the entrance of the erythroblast-staining dye. The second fluid is subsequently added to the mixture of blood sample and the first fluid, whereby the sample solution becomes isotonic and suitable for staining.

The cells thus stained are measured with a flow cytometer and the group of erythroblasts is separated from the other cell groups on the resulting two-dimensional plot and the number of erythroblasts is counted.

The first fluid may also contain the leukocyte-staining and the eosinophil/basophil staining dyes. In this case, not only the differentiation of erythroblasts but also the classification of leukocytes can also be performed since the dyes diffuse into leukocytes to stain their cells.

To state specifically, the method of the present invention is an improvement of the invention described in Unexamined Published Japanese Patent Application No. 282698/1988 (Example 2, 2: 2-step method) and it is illustrated below with reference to working examples. It should, however, be noted that the following examples are in no way intended to limit the present invention.

EXAMPLE 1

Two reagents were prepared to the formulas indicated below. The eosinophil/basophil staining dye in the first fluid was a fluorescent dye that would selectively stain both eosinophils and basophils; the leukocyte-staining dye in the first fluid was a fluorescent dye that would stain the nuclei of leukocytes; and the erythroblast-staining dye in the first fluid was a fluorescent dye that would diffuse into erythroblasts to stain their nuclei.

| First fluid: pH, 4.0; osmorality, 30 mOsm/kg | | |
|---|---|---|
| Eosinophil/Vasophil-staining dye | Basic Yellow 11 | 385 mg/l |
| Leukocyte-staining dye | Astrazon Orange | 330 mg/l |
| Buffer | Diglycolic acid-sodium hydroxide | 10 mM |
| Erythroblast-staining dye | Propidium iodide | 10.5 µg/ml (advantageously 2.5-100 µg/ml) |
| Second fluid: pH, 9.8; osmolarity, 2000 mOsm/kg | | |
| Buffer | Tricin-sodium hydroxide | 300 mM |
| Osmolarity adjusting agent | Sodium chloride | 750 mM |

Using the thus prepared first and second fluids, fluorescence and scattered light were measured for leukocyte classification in the following manner.

First, the blood of a healthy person was made non-clotting and 100 µl of the thus anti-coagulated blood was mixed uniformly with 1800 µl of the first fluid. After agitation, the mixture was incubated at 25° C. for ca. 20 seconds. Thereafter, 200 µl of the second fluid was added and the mixture was agitated, followed by incubation at 25° C. for ca. 40 seconds. The finally obtained sample solution had a pH of 8.6-8.7 and an osmolarity of ca. 280 mOsm/kg (isotonic).

In this way, sample solutions were prepared with the erythrocytes lysed and the various types of leukocytes stained. Those sample solutions were loaded in a flow cytometer for measuring the intensities of fluorescence and scattered light from the leukocytes.

EXAMPLE 2

A measurement was conducted as in Example 1 except that the first fluid contained neither the first nor the second dye. The results of the measurement are shown below. All the samples for measurement were taken from healthy persons.

Figure 2:
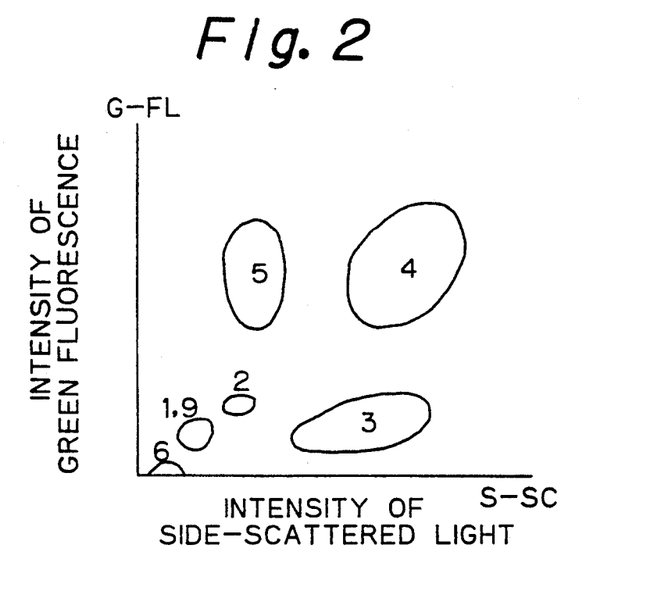
FIG. 2 is a two-dimensional plot for the intensity of green fluorescence (on the vertical axis) as obtained in a measurement using the reagent prepared in Example 1 to be described later in this specification.
Figure 3:
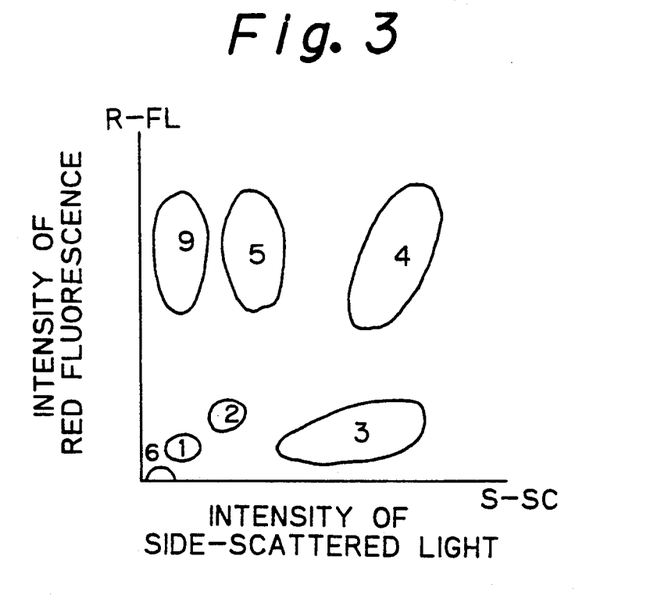
FIG. 3 is a two-dimensional plot for the intensity of red fluorescence (on the vertical axis) as obtained in a measurement on the same sample as in the case of FIG. 2 using the reagent prepared in Example 1.
Figure 4:
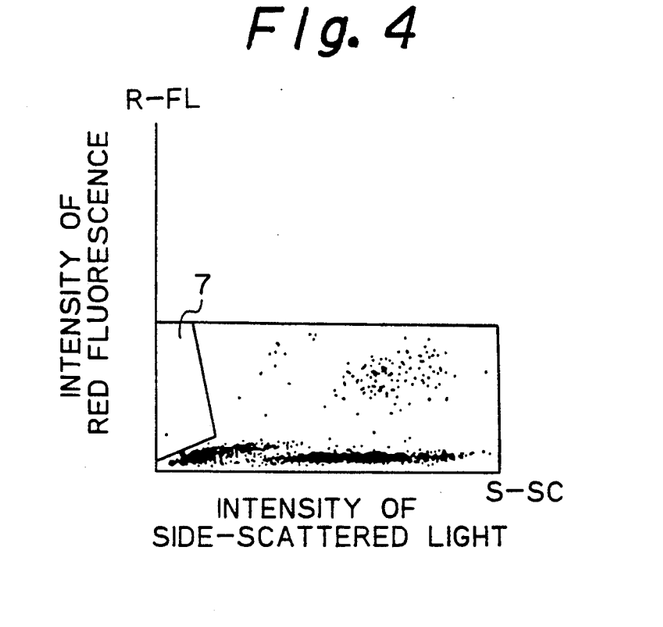
FIG. 4 is a graph showing the actual results of measurement that corresponds to FIG. 3 and that was performed on a peripheral blood sample.
Figure 5:
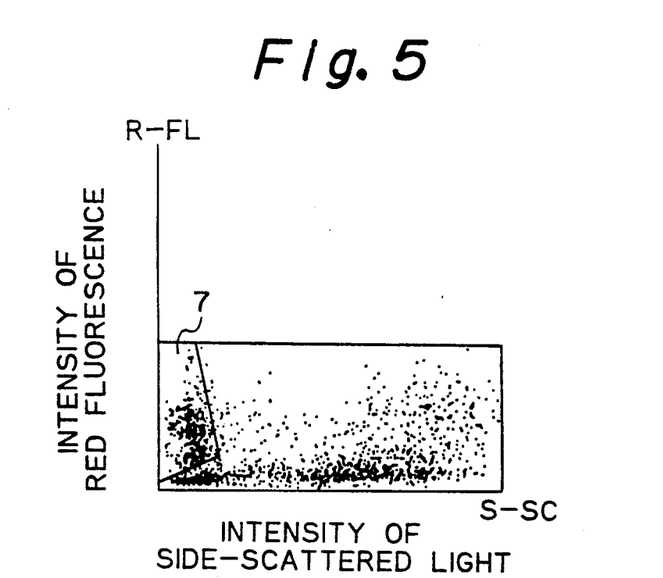
FIG. 5 is a graph showing the actual results of measurement that corresponds to FIG. 3 and that was performed on a sample of bone marrow fluid.
Figure 6:
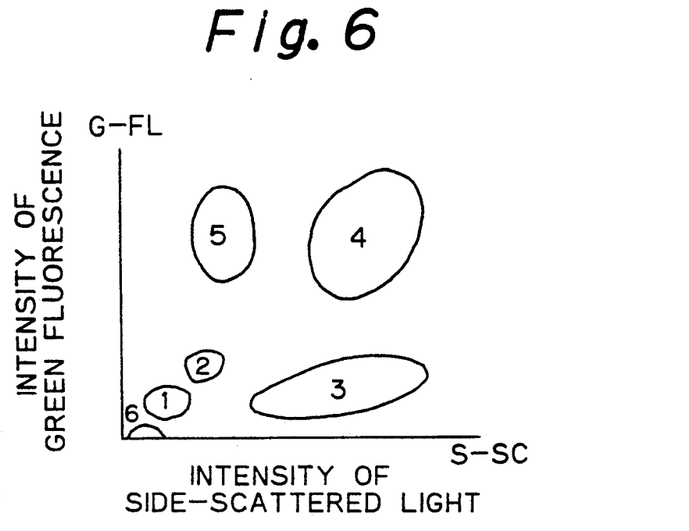
FIG. 6 is a two-dimensional plot for the intensity of green fluorescence vs the intensity of side-scattered light as obtained in a measurement that used the first fluid in the absence of the erythroblast staining dye.
Figure 7:
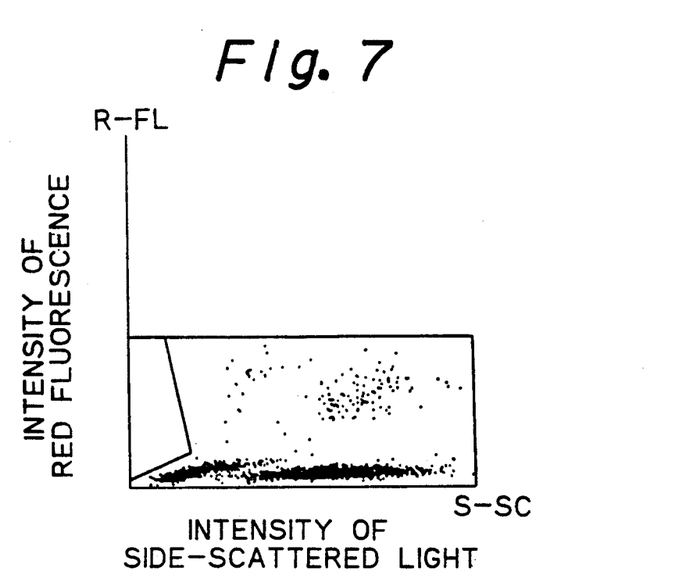
FIG. 7 is a two-dimensional plot for the intensity of red fluorescence vs the intensity of side-scattered light as obtained in a measurement that used the first fluid in the absence of the erythroblast-staining dye and that was performed on a peripheral blood sample.
Figure 8:
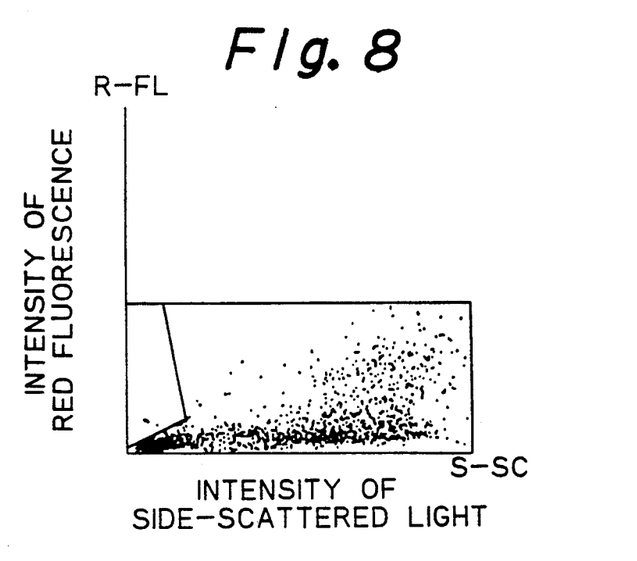
FIG. 8 is a two-dimensional plot for the intensity of red fluorescence vs the intensity of side-scattered light as obtained in a measurement that used the first fluid in the absence of the erythroblast-staining dye and that was performed on bone marrow fluid.
Figure 9:
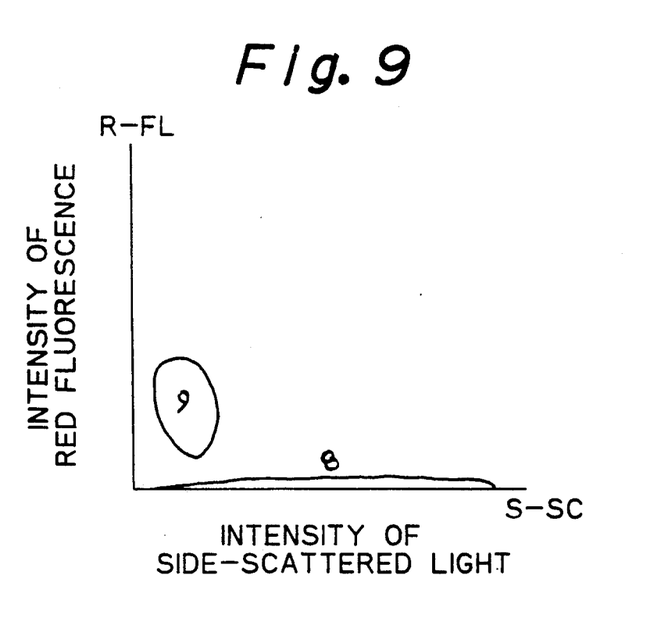
FIG. 9 is a two-dimensional plot that shows the selective staining of erythroblasts with the erythroblast-staining dye to emit red fluorescence.
Figure 10:
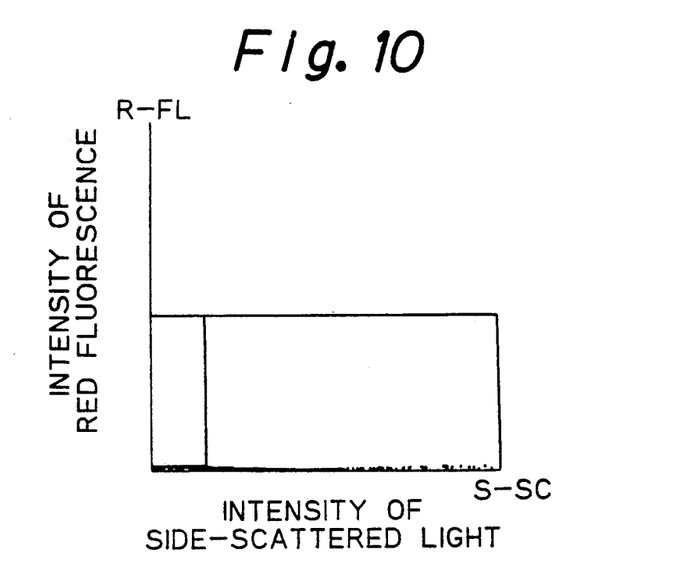
FIG. 10 is a graph showing the actual results of measurement that corresponds to FIG. 9 and that was performed on a peripheral blood sample.
Figure 11:
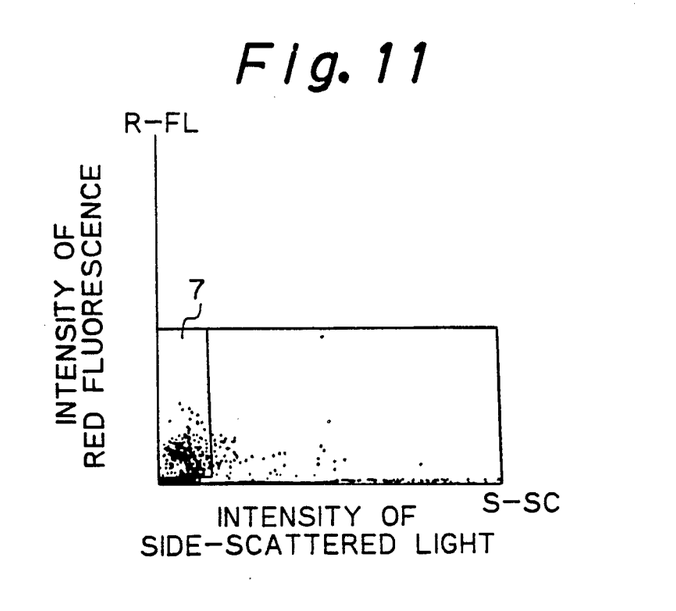
FIG. 11 is a graph showing the actual results of measurement that corresponds to FIG. 9 and that was performed on a sample of bone marrow fluid.

|  | Distribution Pattern | Results of measurement on specimens | |
| --- | --- | --- | --- |
|  |  | Peripheral blood | Bone marrow punctured fluid |
| Method of Example 1 | FIGS. 2 and 3 | FIG. 4 | FIG. 5 |
| Prior art Method | FIG. 6 | FIG. 7 | FIG. 8 |
| Method of Example 2 | FIG. 9 | FIG. 10 | FIG. 11 |

FIG. 6 is a two-dimensional plot of the intensity of green fluorescence vs the intensity of side-scattered light as obtained when measurements were conducted using the prior art reagent namely the first fluid not containing the erythroblast-staining dye. Numerals 1–6 in the plot signify the distribution zones of lymphocytes, monocytes, neutrophils, eosinophils, basophils and erythrocyte ghost, respectively. (A two-dimensional plot of the intensity of red fluorescence vs the intensity of side-scattered light was found to show the same pattern of distribution.)

FIGS. 7 and 8 are two-dimensional plots of the intensity of red-fluorescence vs the intensity of side-scattered light actually obtained when measurements were conducted using the prior art reagent, that is a reagent not containing the erythroblast-staining dye. The sample used in FIG. 7 comprised peripheral blood not containing erythroblasts and that of FIG. 8 was bone marrow punctured fluid containing erythroblasts. Neither FIG. 7 nor FIG. 8 indicates plots of erythroblasts. Even if the intensity of green fluorescence used in these figures were replaced by that of red fluorescence, erythroblasts cannot be detected as long as the prior art reagent is used. Detection of erythroblasts is possible only when a reagent containing the erythroblast-staining dye is used and the intensities of red fluorescence are measured (FIGS. 4, 5, 10 and 11). In other words, even if a reagent containing the erythroblast-staining dye is used, erythroblasts cannot be detected by measuring the intensity of green fluorescence.

FIGS. 2 and 3 are two-dimensional plots obtained when measurements were conducted on the same sample using the reagents prepared in Example 1; the respective graphs plot the intensities of green and red fluorescence on the vertical axis. Shown by 9 in each graph is the distribution zone of erythroblasts. FIGS. 4 and 5 are graphs showing the actual results of measurement that correspond to FIGS. 2 and 3, respectively.

Since the sample used was derived from the peripheral blood of healthy persons which did not contain erythroblasts, FIG. 4 (Example 1) and FIG. 7 (the prior art method) showed almost the same distribution pattern.

FIGS. 5 and 8 are two-dimensional plots as obtained when measurements were conducted on a sample fluid obtained from bone marrow. The bone marrow fluid contains many erythroblasts. With the aid of the hypotonic and acidic first fluid containing the erythroblast-staining dye, erythrocytes in the blood are lysed whereas the nucleated erythroblasts are stained with the erythroblast-staining dye to emit red fluorescence. The leukocytes are stained with the eosinophil/basophil-staining and leukocyte-staining dyes to emit red and green fluorescence. However, the erythroblasts and leukocytes appear in different zones of the two-dimensional plot. Hence, there is no difficulty in separating the erythroblasts from the leukocytes on the two-dimensional plot. It is also possible to classify the leukocytes into five different types.

As shown in FIG. 5, the method of the present invention allowed erythroblasts to appear in zone 7 of red fluorescence, which was impossible in the prior art method (FIG. 8).

In Example 2, Basic Yellow 11 (first dye) and Astrazon Orange R (second dye) were eliminated from the first fluid, which hence contained only the erythroblast-staining dye. The method of preparation of the first fluid was otherwise the same as in Example 1.

FIG. 9 is a two-dimensional plot showing the selective staining of erythroblasts 9 with the erythroblast-staining dye to emit red fluorescence. Shown by 8 are the other corpuscles. FIGS. 10 and 11 are two-dimensional plots for the intensity of red fluorescence vs the intensity of side-scattered light, as obtained when peripheral blood and bone marrow fluid were respectively used as samples. In the absence of erythroblasts from the sample (peripheral blood), no signal for red fluorescence appeared in FIG. 10. FIG. 11 shows that only erythroblasts emitted fluorescence when the sample was a bone marrow punctured fluid. As in Example 1, erythroblasts appeared in zone 7 but there was no appearance of leukocytes. Hence, the erythroblasts count can be obtained by counting the number of corpuscles in zone 7. In other words, it was possible to differentiate and count erythroblasts with the aid of the erythroblast-staining dye alone.

When the eosinophil/basophil-staining and leukocyte-staining dyes were also contained in the first fluid as in Example 1, not only could erythroblasts be differentiated but also the leukocytes could be classified into five different types as described in Example 1.

Using the first fluid which contains the erythroblast-staining dye, the method of the present invention permits erythroblasts to be distributed on a two-dimensional plot in a different zone than are the other cell types and this enables the relative content and count of erythroblasts to be determined with high precision.

If the eosinophil/basophil-staining and leukocyte-staining dyes are also contained in the first fluid, the classification of leukocytes can be performed simultaneously with the differentiation of erythroblasts.

What is claimed is:

1. A method of differentiating erythroblasts from other cells by flow cytometry which comprises the following steps:
    (a) a first step of forming a first sample fluid by mixing a sample of body fluid with a first hypotonic fluid comprising a dye for specifically staining erythroblasts that is a fluorescent dye capable of diffusing into erythroblasts to stain their nuclei and a buffer for maintaining an acidic pH;
    (b) a second step of forming a second sample fluid by mixing the first sample fluid obtained in step (a) with a second sample fluid comprising a buffer for maintaining the pH of the second sample fluid at a staining pH and an osmolarity adjusting agent for adjusting the osmolarity of the second sample fluid to a value at which leukocytes remain unchanged in shape;

(c) then loading the second sample fluid in a flow cytometer and obtaining at least one signal for parameters including fluorescence and scattered light in association with individual cell types;

(d) constructing a two-dimensional plot of the intensities of fluorescence and scattered light from the detected signals; and (e) differentiating a distribution zone of erythroblasts on the constructed two-dimensional plot and counting the number of cells in that zone.

2. A method according to claim 1 wherein the dye for staining erythroblasts is selected from the group consisting of Propidium iodide, Etidium bromide and N-methyl-4-(1-pyrene)vinyl-Propidium iodide.

3. A method according to claim 1 wherein the first hypotonic fluid further comprises a dye for staining basophils and eosinophils that is a fluorescent dye capable of selectively staining eosinophils and basophils and a dye for staining leukocytes that is a fluorescent dye capable of staining nuclei of all leukocytes.

4. A method according to claim 3 wherein the eosinophil/basophil-staining dye is Astrazon Yellow 3G.

5. A method according to claim 3 wherein the leukocyte-staining dye is selected from the group consisting of the following members:
Acridine Red;
Rhodamine S;
Rhodamine 6G;
Rhodamine B;
Rhodamine 19 perchlorate;
Rhodamine 123;
Eosin Y;
Cyanosine;
Cresyl Fast Violet;
Darrow Red;
Acronol Phloxine FFS;
1,1'-dimethylthiocarbocyanine;
1,1'-diethylthiocarbocyanine;
1,1'-diethyl-9-methylthiocarbocyanine bromide;
2-[γ-(1'-ethyl-4',5'-benzothiazolylidene)propenyl]-1-ethyl-4,5-benzoxazolium iodide;
Astrazon Red 6B;
Basic Violet 16;
2-(p-dimethylaminostyryl)-1-ethyl-4,5-benzothiazolium iodide;
2,4-bis(p-dimethylaminostyryl)-1-ethylpyridinium iodide;
2,6-bis(p-dimethylaminostyryl)-1-ethylpyridinium iodide; and
Astrazon Orange R.

6. A method according to any one of the preceding claims wherein the two-dimensional plot is that of the intensities of side-scattered light and red fluorescence.

* * * * *